Figure 1:
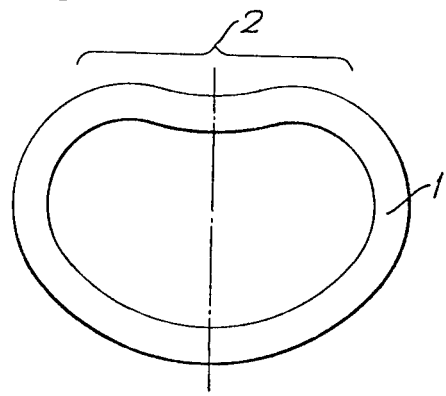

United States Patent [19]

Carpentier et al.

[11] 4,055,861
[45] Nov. 1, 1977

[54] SUPPORT FOR A NATURAL HUMAN HEART VALVE

[75] Inventors: Alain Carpentier, Paris; Xavier Leclercq, Orgeval; Jean Paris, Saint-Denis, all of France

[73] Assignee: Rhone-Poulenc Industries, Paris, France

[21] Appl. No.: 675,592

[22] Filed: Apr. 9, 1976

[30] Foreign Application Priority Data

Apr. 11, 1975 France .................... 75.11361

[51] Int. Cl.$^2$ .................... A61F 1/22; A61F 1/24
[52] U.S. Cl. .................... 3/1.5
[58] Field of Search .................... 3/1.5, 1; 128/334 R

[56] References Cited

U.S. PATENT DOCUMENTS

| | | |
|---|---|---|
| 3,579,642 | 5/1971 | Heffernan et al. .................... 3/1.5 |
| 3,656,185 | 4/1972 | Carpentier .................... 3/1.5 |
| 3,839,741 | 10/1974 | Haller .................... 3/1.5 |

Primary Examiner—Ronald L. Frinks
Attorney, Agent, or Firm—Stevens, Davis, Miller & Mosher

[57] ABSTRACT

A support for a natural human heart valve is disclosed, said support consisting of an annular or part annular semi-rigid frame having the shape of at least a substantial portion of the periphery of said natural heart valve at the base of its cusps, the frame being completely or partly enclosed in a textile sheath, the frame and the sheath being formed of a bio-compatible material and being deformable after implantation. The frame and sheath may be flexurally deformable, and are extensible by 0.001 times to 0.3 times their length. Preferably, the frame has the same flexural elasticity as an annular bundle or 2 to 8 turns of a cylindrical bristle or poly(ethylene terephthalate) and having a circumference equal to 0.025 times the length of one turn. The frame may be formed of at least one strand of bristle. The frame and the sheath may be in the form of a portion of a convex curve.

9 Claims, 2 Drawing Figures

SUPPORT FOR A NATURAL HUMAN HEART VALVE

The present invention relates to a support for a natural human heart valve which may be used for the surgical non-mutilating correction of malformations of the valve cusps, especially in cardiology.

British Pat. No. 1,293,014 describes an annular or part annular valve support which fits the base of the valve cusps and consists of a rigid frame, means of suturing and a textile sleeve. Though this implantable support proves satisfactory in a large number of cases, it has been found that its rigidity could in the long term alter the free play of the cusps and give rise to detachment of the support. Furthermore, this support is inextensible which means that if it is used in a child or an adolescent successive operations must be carried out from time to time to change the support as the patient grows, until the patient is adult.

According to the present invention there is provided a support for a natural human heart valve, such support consisting of an annular or part annular semi-rigid frame having the shape of at least a substantial portion of the periphery of said natural heart valve at the base of its cusps, the frame being completely or partly enclosed in a textile sheath, the frame and the sheath being formed of a bio-compatible material and being deformable after implantation.

Figure 2:
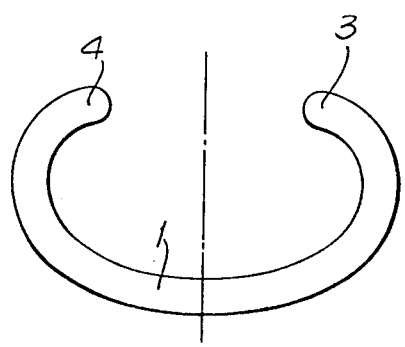

Such a support may deform periodically in accordance with the cardiac contraction rhythm and under the stimulus from the adjacent tissues, and is capable of extension. In order that the invention will be still better understood, the following description is given merely by way of example, reference being made to the accompanying drawing, in which:

FIG. 1 is an elevation of one embodiment of support according to the invention in the form of a ring; and FIG. 2 is an elevation of another embodiment of support according to the invention which is part annular. The valve supports according to the invention represented in FIGS. 1 and 2 are at rest, that is to say they have not yet been implanted and hence have not undergone any deformation caused by the adjacent tissues in which they will be implanted.

The support 1 shown in FIG. 1 tightly fits the base of the cusps of the heart valve and is substantially in the form of a ring. This support, at rest, is planar, circular, oval, or preferably, slightly flattened at 2 over a length which is between a quarter and half of its circumference (see FIG. 1). The zone 2 corresponds to the curvature of the large cusp and the supplementary zone corresponds to the curvature of the small cusp of a heart valve. The support may have an axis of symmetry in its plane; its largest dimensions, along this axis and along an axis at right angles thereto, are generally respectively between 15 and 30 mm and between 18 and 40 mm. The thickness of the support, taken at right angles to its plane when it is in its rest condition as shown, is between 1 and 6 mm and preferably between 2 and 4 mm.

In certain cases it has been found that it may be advantageous to maintain certain cusps while preserving the free play of one valve (for example the large cusp in the case of the mitral valve). Hence, a support according to the embodiment shown in FIG. 2 also forms a part of the present invention.

The support 1 according to FIG. 2 has the shape of a portion of a convex slightly flattened curve, so as to fit tightly the base of the cusps. This support is open over a distance which is generally between a quarter and half of its length. This distance corresponds substantially to the dimension of the base of the cusp to which it is desired to allow free play. Thus, in FIG. 2 the support is open over a distance equal to one-third of its length, this distance corresponding substantially to the base of the large cusp. The support thus tightly fits the base of the small cusp and allows free play of the large cusp.

It is also possible to produce a support of which the open portion corresponds substantially to the base of the small cusp and which tightly fits the base of the large cusp and thus allows free play of the small cusp.

The extremities 3 and 4 of the support according to the embodiment of FIG. 2 are rounded off so as not to injure the tissues in which they are placed.

The dimensions of a support in the form of a portion of a convex curve are similar to the dimensions of an annular support.

The support according to the present invention consists of a frame surrounded at least partially, and preferably entirely, by a textile sheath. The frame is flexurally deformable, to an equal degree and simultaneously in all the directions within its rest plane and outside the latter, so as to assume the form of a skew curve.

Preferably, the elasticity of the support is the same as the flexural elasticity of an annular bundle of 2 to 8 turns of a cylindrical bristle, the bristle being of poly (ethylene terephthalate) and having a circumference equal to 0.025 times the length of one turn (which, in the case of a toroidal support, means that the diameter of the bristle is equal to 0.25 times the large diameter of the toroid).

Bristle is to be understood here as meaning a continuous monofilament of which the cross-section is substantially constant and the area of the cross-section of which is greater than 0.01 mm$^2$. The shape of the cross-section is not critical. It is generally circular but may also, for example, be elliptical (ratio of major axis to minor axis preferably less than 3), ovoid, or a curvilinear polygon.

The frame of an annular support may be formed of one or more turns of a single bristle or of a bundle of strands of bristles. The extremities of the bristles may be fixed by welding, glueing or ligature, in such a way as to prevent them sticking out. In the text which follows, strand of bristle will be understood to mean finished lengths of bristle cut, for example, from a bristle wound up on a bobbin.

The extremities are preferably rounded, for example, by melting, molding or coating.

The various turns may simply be juxtaposed or, on the other hand, they may be interlaced so as to render them more coherent.

As a variant, the frame may consist of a toroidal bristle or of a juxtaposition of strands of toroidal bristles, produced for example by molding. A single bristle may be rolled up into a helix similarly to a helical spring, and will then be shaped in the form of a ring or a portion of a convex curve.

The frame of a part-annular support may be formed analogously. This frame can be obtained from a frame blank, in the form of a ring, which is cut, with or without removal of a part of its length. The free ends of the bristles are then fixed to one another by welding, glueing or ligature, in such a way as to prevent them sticking out. Preferably, the free ends are rounded, for example by melting, molding or coating.

The frame may initially be shaped by molding (especially in the case of the toroidal bristles) or it may be shaped at a later stage by a heat treatment on a former.

In that case, it is possible to shape either a finished frame or a length of bristle corresponding to several frames.

In general, frames which comprise at least two turns of a single bristle or at least two strands are preferred, because in this way the implant can be sutured by stitches which pass between the turns or between the strands of the main body of the support. This facilitates the surgeon's work.

Covering the frame with a textile sheath does not present any particular problems and is a per se well known technique. This sleeve or sheath contributes to the cohesion of the bundle of bristles, to the fixing of the support by suture, and to its incorporation into the connective tissue.

The textile sheath is in general a woven fabric, for example a napped fabric or a cut velour. It may also be a knitted or braided sleeve. The sleeve may also optionally be made of a non-woven fabric.

It is possible to produce extensible supports for heart valves according to the invention. The increase in length of the support can be between 0.001 times and 0.3 times its length, and preferably between 0.01 times and 0.25 times its length.

The extensibility of the support may be achieved by the choice of materials of which the frame consists, that is to say by the choice of the material of which the bristle used to produce the frame consists.

It is also possible to produce supports in the form of extensible rings by constructing their frame from a single bristle of which the ends are brought together by means of a sleeve in which they may slide.

It is also possible to produce an extensible support by using, as the frame, a single bristle twisted into coaxial helical turns, as has been described above.

The frame and the sheath may be produced with the aid of any inert materials which are well tolerated by the organism and exhibit the necessary mechanical properties.

As the material it is possible to choose polyesters such as poly(ethylene terephthalate) or poly (glycol terephthalate), polyamides such as nylon 6—6, nylon 11 or nylon 12, polyolefins, especially polypropylene, fluorinated polymers such as polytetrafluoroethylene, or polyvinyl chloride.

The textile sheath may also consist of natural and/or artificial fibers which may be combined with synthetic fibers of materials as defined above.

The support according to the present invention may optionally comprise at least one radio-opaque element. This radioopaque element may be one bristle of the frame, or the entire frame itself, or the whole or a part of the textile sheath. As the radio-opaque material, it is possible to use especially compounds which contain heavy metals such as barium or bismuth.

The textile sheath optionally comprises a colored thread, located in a plane parallel to the plane of rest of the support. This colored thread allows the surgeon to orient the support while it is being placed in position.

It is to be understood that the combination with one another of two or more embodiments of the support according to the present invention is also possible.

The support according to the present invention exhibits numerous advantages. In fact, its flexibility exhibits the advantage that it avoids long-term alteration of free play of the cusps. Furthermore, the support deforms periodically in accordance with the cardiac contraction rhythm and under the stimulus of the adjacent tissues, and thus any lesion of the myocardium in the vicinity of the support is virtually avoided.

Such supports follow particularly well all the deformations of the valvular apparatus, in accordance with the cardiac contraction rhythm.

The examples which follow further illustrate the invention but without limiting it.

EXAMPLE 1

A coil of adjacent turns of a bristle of poly(ethylene terephthalate) of diameter 0.60 mm is produced on a former of which the cross-section is the same as that of a tricuspid valve and of which the circumference measures 88 mm. After heat-fixing, a length corresponding to 3.05 turns is cut off. The two extremities are melted to round them off and the two end sections are glued side by side over a length of about 5 mm.

The thus-formed frame is covered with a strip of jersey tricot made of a continuous multi-filament yarn of the same polyester, the edges being folded inwardly before making an overcast sewing seam along one generatrix.

EXAMPLE 2

Example 1 is repeated, this time using 5 turns of a bristle of the same polyester of 0.45 mm diameter.

What is claimed is:

1. A support for a natural human heart valve, said support consisting of a partannular semi-rigid frame defining a longitudinal axis along its length and having the shape of at least a substantial portion of the periphery of said natural heart valve at the base of its cusps, the frame being at least partly enclosed in a textile sheath, the frame and the sheath being flexurally deformable in all directions about the longitudinal axis of the frame and formed of a biocompatible material.

2. A support according to claim 1, wherein the frame and the sheath are extensible by 0.001 times to 0.3 times their length.

3. A support according to claim 1, wherein the frame has the same flexural elasticity as an annular bundle of 2 to 8 turns of a cylindrical bristle of poly(ethylene terephthalate) having a circumference equal to 0.025 times the length of one turn.

4. A support according to claim 1, wherein the frame is formed of at least one strand of bristle.

5. A support according to claim 1, wherein the frame and the sheath are in the form of a portion of a convex curve.

6. A support according to claim 5, wherein the distance between the extremities of the said portion of the convex curve is between one quarter and one half the length of the said portion.

7. A support according to claim 1, wherein the frame and the sheath are in the form of an annular ring.

8. A support according to claim 7, wherein the frame is formed of at least two turns of a bristle.

9. A support for a natural human valve, said support consisting of an elongated flexurally deformable frame having a longitudinal axis curved along its length to define a generally ring-shaped frame having the shape of at least a substantial portion of the periphery of a natural heart valve at the base of its cusps, said frame being substantially enclosed in a textile sheath, said frame and sheath being formed of biocompatible material and being flexurally deformable in all directions about said longitudinal axis.

* * * * *